US006942473B2

(12) United States Patent
Abrahamson et al.

(10) Patent No.: US 6,942,473 B2
(45) Date of Patent: Sep. 13, 2005

(54) PUMP AND TUBE SET THEREOF

(75) Inventors: Kent Abrahamson, Morgan Hill, CA (US); Colm Clinton, Cairns Road (IE); Brendan Duggan, Co. Sligo (IE); Ricky Fabozzi, Sligo (IE); Damian Halloran, Evanston, IL (US); Philip O'Donnell, Co. Sligo (IE); Barry Regan, Chicago, IL (US)

(73) Assignee: Hospira, Inc., Lake Forest, IL (US)

( * ) Notice: Subject to any disclaimer, the term of this patent is extended or adjusted under 35 U.S.C. 154(b) by 486 days.

(21) Appl. No.: 10/063,110

(22) Filed: Mar. 21, 2002

(65) Prior Publication Data

US 2003/0181866 A1 Sep. 25, 2003

(51) Int. Cl.[7] .................................. F04B 43/12
(52) U.S. Cl. ..................... 417/474; 417/477.2; 604/153
(58) Field of Search ........................ 417/474, 477.2, 417/477.12, 479; 604/153

(56) References Cited

U.S. PATENT DOCUMENTS

| 4,302,164 A | 11/1981 | Manella |
| 4,382,753 A | 5/1983 | Archibald |
| 4,424,009 A | 1/1984 | van Os |
| 4,479,797 A | 10/1984 | Kobayashi et al. |
| 4,496,351 A | 1/1985 | Hillel et al. |
| 4,558,989 A | 12/1985 | Chappel |
| 4,559,038 A | 12/1985 | Berg et al. |
| 4,565,542 A | 1/1986 | Berg |
| 4,586,691 A | 5/1986 | Kozlow |
| 4,650,469 A | 3/1987 | Berg et al. |
| 4,671,792 A * | 6/1987 | Borsanyi ..................... 604/153 |
| 4,689,043 A | 8/1987 | Bisha |
| 4,731,058 A | 3/1988 | Doan |
| 4,781,548 A | 11/1988 | Alderson et al. |
| 4,811,928 A | 3/1989 | Iwatschenko et al. |
| 4,886,431 A | 12/1989 | Soderquist et al. |
| 4,890,984 A | 1/1990 | Alderson et al. |
| 4,893,991 A | 1/1990 | Heminway et al. |
| 4,909,710 A | 3/1990 | Kaplan et al. |
| 4,936,760 A | 6/1990 | Williams |
| 4,950,245 A | 8/1990 | Brown et al. |
| 5,017,059 A | 5/1991 | Davis |
| 5,151,019 A | 9/1992 | Danby et al. |
| 5,199,852 A | 4/1993 | Danby |
| 5,213,483 A * | 5/1993 | Flaherty et al. .......... 417/477.2 |
| 5,346,466 A | 9/1994 | Yerlikaya et al. |
| 5,364,242 A | 11/1994 | Olsen |
| 5,397,222 A * | 3/1995 | Moss et al. .............. 417/477.2 |
| 5,437,635 A | 8/1995 | Fields et al. |
| 5,453,098 A | 9/1995 | Botts et al. |
| 5,531,697 A | 7/1996 | Olsen et al. |
| 5,564,915 A | 10/1996 | Johnson |

(Continued)

FOREIGN PATENT DOCUMENTS

| EP | 0 510 881 | 4/1992 |
| EP | 0 483 794 | 9/1994 |
| EP | 0 423 978 | 1/1995 |
| WO | 96 27402 | 9/1996 |
| WO | 98 56441 | 12/1998 |
| WO | 98 56453 | 12/1998 |

Primary Examiner—Michael Koczo, Jr.
(74) Attorney, Agent, or Firm—Michael R. Crabb

(57) ABSTRACT

A pump includes a housing defining a tube receiving portion and a blade mounted for reciprocating movement between first and second positions. In its first position, the leading edge of the blade compresses a length of tube against a first surface disposed in the tube-receiving portion, while in the second position, the blade does not compress the tube. The tube-receiving portion can receive the tube directly or indirectly through a tube set detachably mounted to the housing. The tube set includes a tube and a base having first and second end portions that respectively define first and second tube-receiving apertures for slidably receiving a length of the tube therethrough. The base has a first surface constructed to engage the length of tube between the apertures for compression by the pump blade.

7 Claims, 5 Drawing Sheets

U.S. PATENT DOCUMENTS

| | | |
|---|---|---|
| 5,567,136 A | 10/1996 | Johnson |
| 5,575,632 A | 11/1996 | Morris et al. |
| 5,647,854 A | 7/1997 | Olsen et al. |
| 5,658,252 A | 8/1997 | Johnson |
| 5,772,409 A * | 6/1998 | Johnson ................ 417/474 |
| 5,823,746 A * | 10/1998 | Johnson ................ 417/474 |
| 5,879,144 A | 3/1999 | Johnson |
| 5,964,583 A * | 10/1999 | Danby ................ 604/153 |
| 6,056,522 A * | 5/2000 | Johnson ................ 417/474 |

* cited by examiner

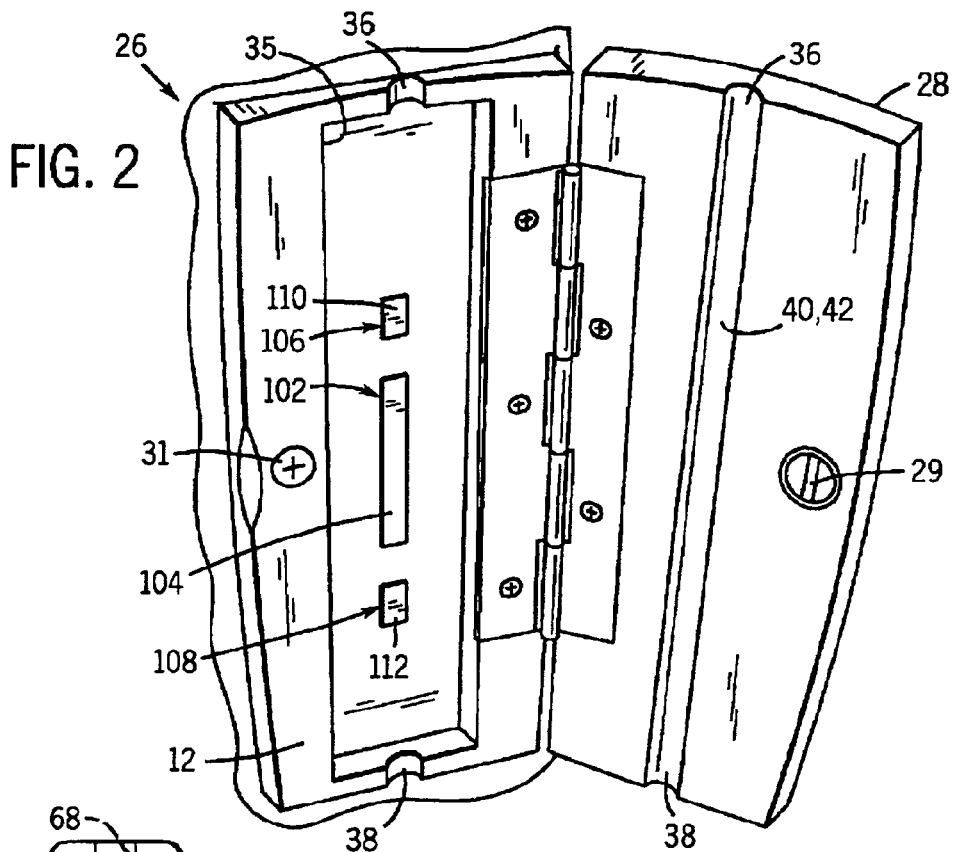
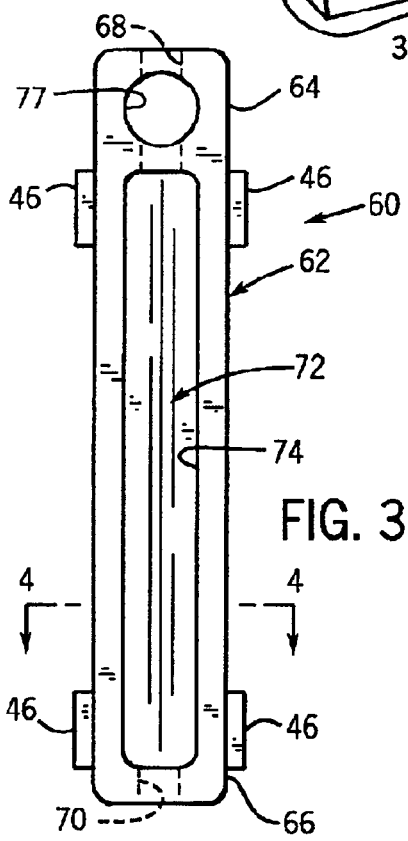
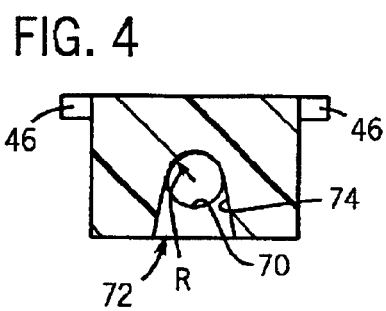
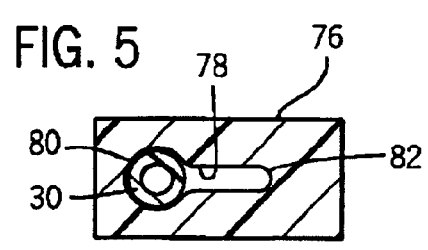

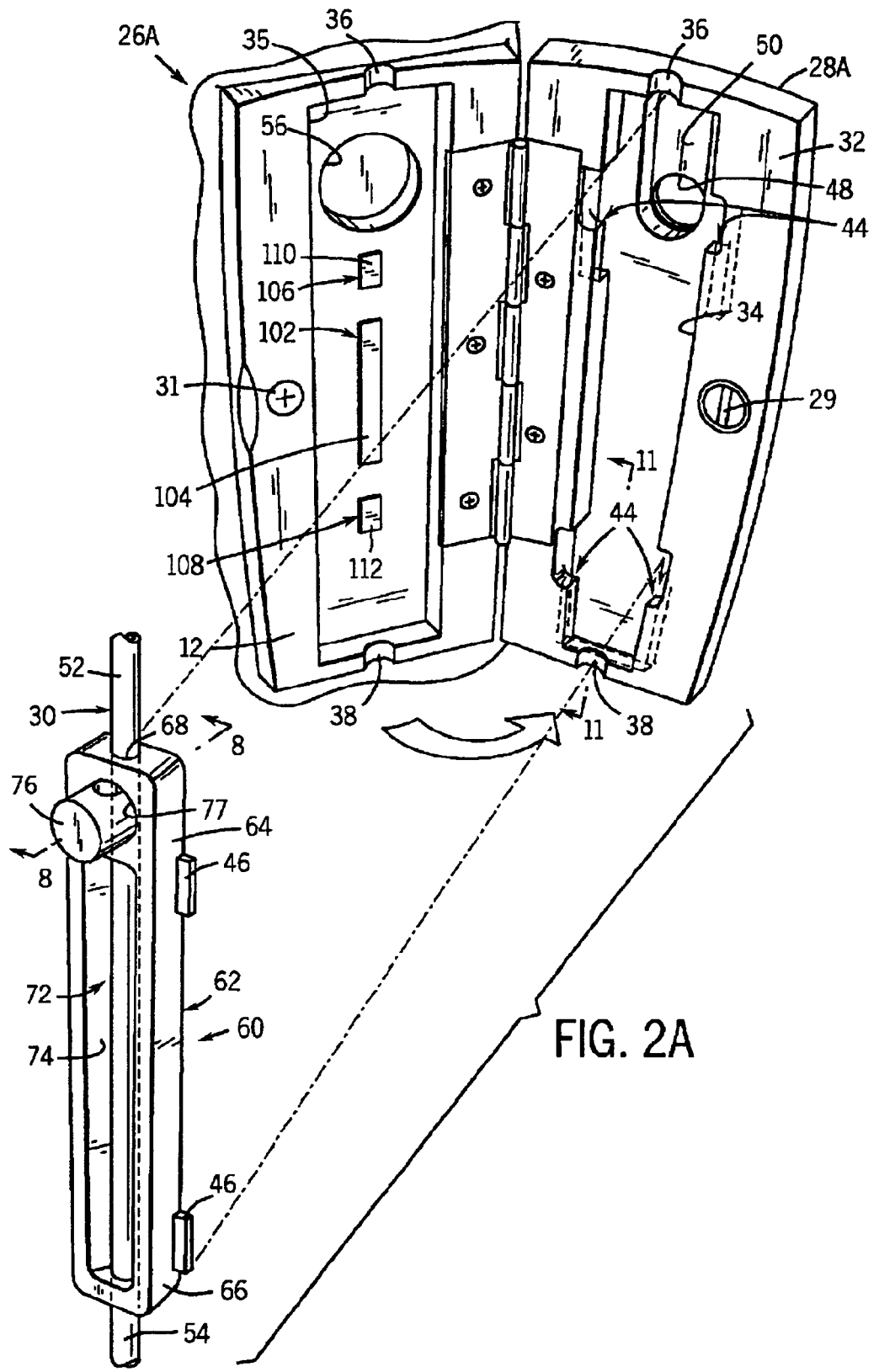

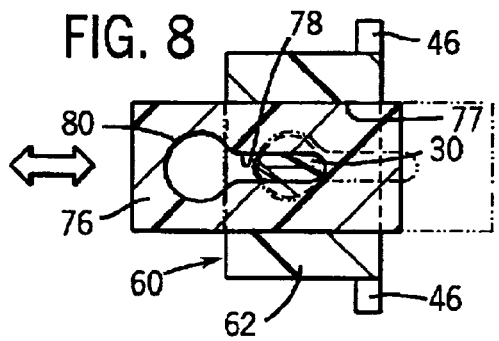
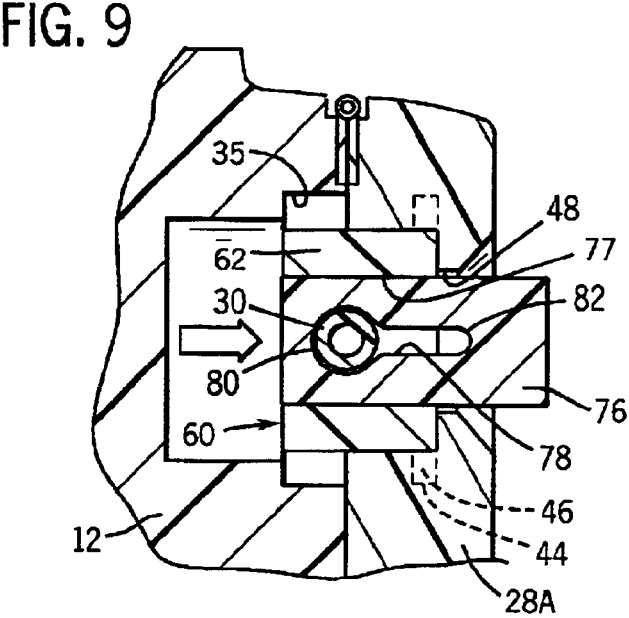
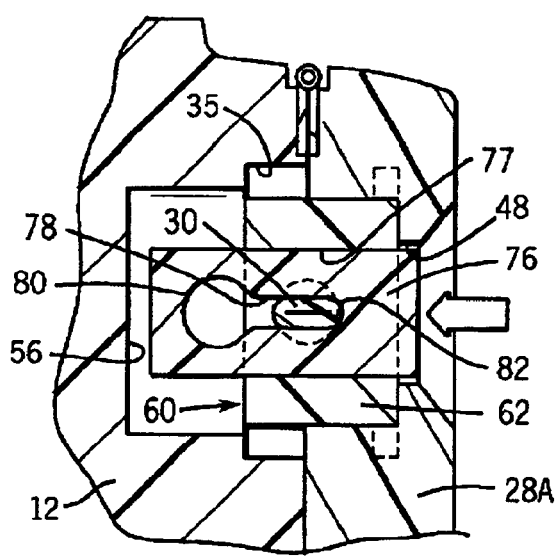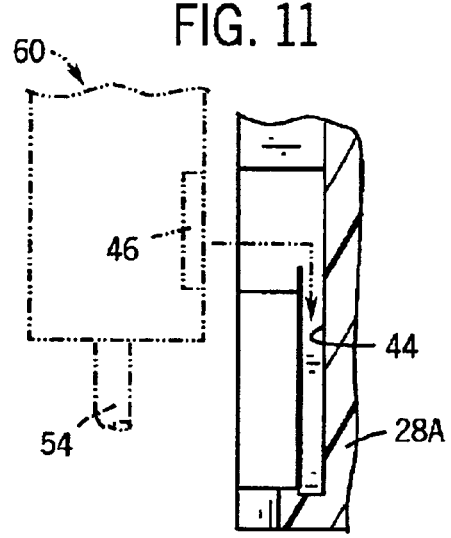

PUMP AND TUBE SET THEREOF

BACKGROUND OF INVENTION

The present invention relates generally to a pump and a tube set therefor, and more particularly to a pump constructed to deliver an enteral or parenteral fluid to a patient, and a tube set constructed for use with the pump.

SUMMARY OF INVENTION

The present invention relates to a pumping mechanism having a tube-receiving portion constructed to receive and constrain a length of tube therein. The tube-receiving portion defines a lengthwise channel therein, the channel being substantially parallel to a length of tube received within the tube-receiving portion. The pumping mechanism further includes a blade having a leading portion having a length and a width, the length of the leading portion of the blade being greater than its width. The leading portion of the blade is constructed to engage, along its length and width, a length of tube disposed in the tube-receiving portion. The blade is mounted for reciprocating movement between a first position and a second position. When the blade is in its first position, the leading portion of the blade compresses a length of tube disposed in the tube-receiving portion, the length of tube compressed being substantially equal to the length of the leading portion of the blade. When the blade is in its second position, the leading portion of the blade is in a position in which it does not substantially compress a length of tube disposed in the tube-receiving portion. The pump further includes a reciprocator constructed to move the blade between its first and second positions.

In one embodiment of the pump of the present invention, the pump further includes a first occlusion member positioned upstream from the blade and a second occlusion member positioned downstream from the blade. In this embodiment, the reciprocator is further constructed to move the first and second occlusion members between first and second positions. In their respective first positions, the first and second occlusion members substantially occlude flow through said tube. In their respective second positions, the first and second occlusion members do not occlude flow through the tube. In this embodiment, the reciprocator is configured to provide a desired coordinated sequencing of movements of the blade, the first occlusion member, and the second occlusion member between their respective first and second positions in order to impart a desired flow pattern through the tube.

The present invention also relates to a tube set including a tube and a base or tube holder having a first end portion and a second end portion. The first end portion of the base defines a first tube-receiving aperture therethrough, and the second end portion of the base defines a second tube-receiving aperture therethrough. The first and second tube-receiving apertures are constructed to slidably receive the tube therethrough. The base defines a channel therein, the channel extending between the first and second end portions of the base. The channel is defined by a surface of the base constructed to engage a length of tube about a portion of the circumference of the tube. At least a portion of the tube is constructed to be compressed against the surface of the base by a blade associated with a pump with which the tube set is used.

BRIEF DESCRIPTION OF DRAWINGS

For a more complete understanding of the present invention, reference may be had to the following Detailed Description read in connection with the accompanying drawings in which:

FIG. 2 is a perspective view of a tube-receiving portion of a pump constructed in accordance with one embodiment of the present invention;

FIG. 2A is an exploded view of a tube set and tube set receiving portion of a pump constructed in accordance with another embodiment of the present invention;

FIG. 3 is a front elevation plan view of a tube holder base of a tube set constructed in accordance with the present invention;

FIG. 4 is a lateral cross-sectional view of the tube holder taken along line 4—4 in FIG. 3;

FIG. 5 is a longitudinal cross-sectional view of the slide clamp with a tube inserted therein in accordance with the present invention;

FIG. 8 is a cross-sectional view taken along line 8—8 in FIG. 2A and shows the slide clamp moved to a position where it occludes the tube in the tube holder;

FIG. 9 is a partial cross-sectional view similar to FIG. 8 but shows the tube set installed on the pump and the slide clamp moved to a non-occluding position;

FIG. 10 is a partial cross-sectional view similar to FIG. 9 but shows the slide clamp moved to a position where it occludes the tube; and FIG. 11 is a partial cross-sectional view taken along line 11—11 in FIG. 2A and shows in greater detail the structure for slidably mounting the tube set on the tube set receiving portion of the pump in accordance with the present invention.

DETAILED DESCRIPTION

Figure 1:
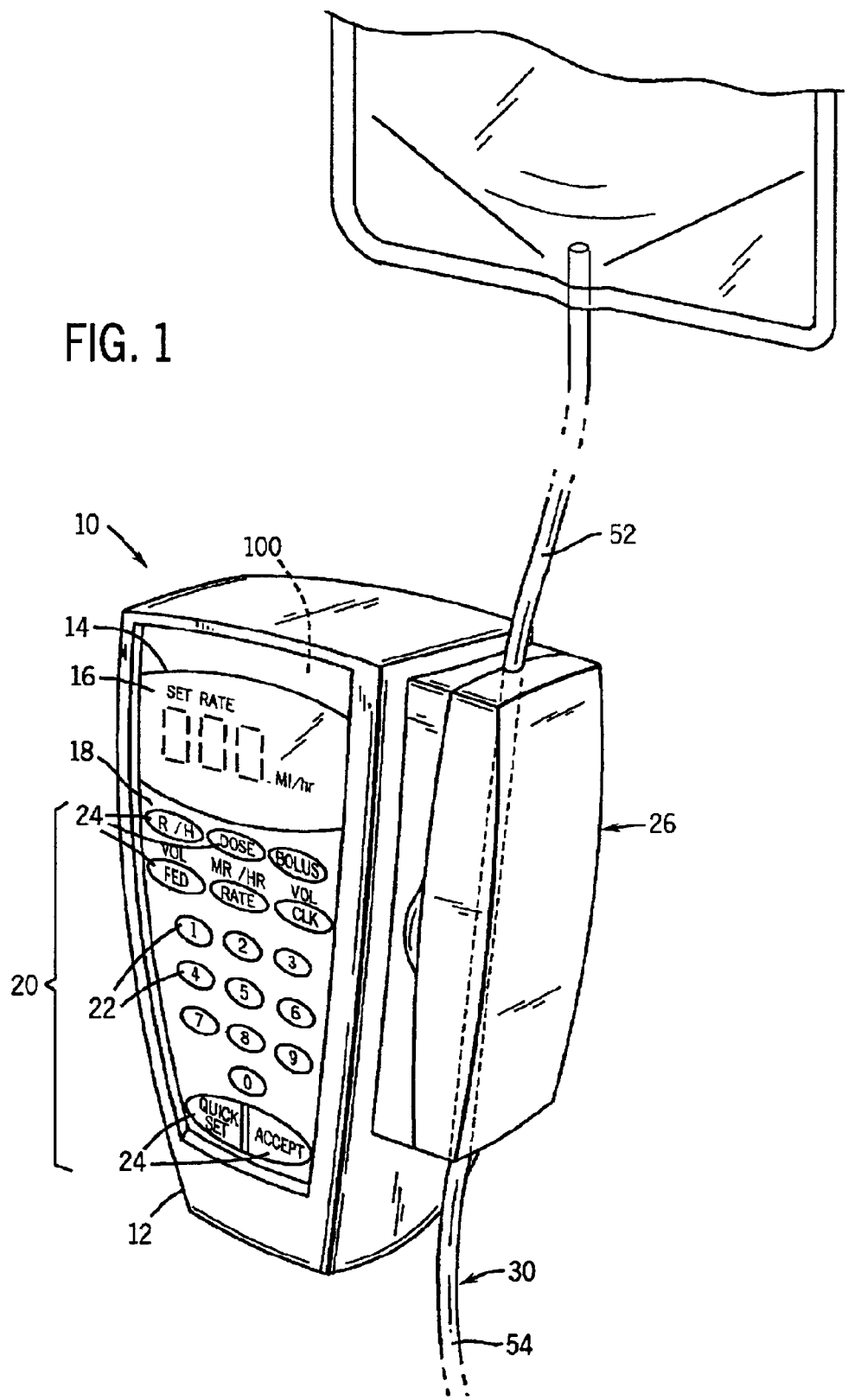
FIG. 1 is a perspective view of a pump constructed in accordance with the present invention.

Features or elements that are the same or similar in structure or function are designated with the same or similar reference numerals in the figures and the following description.

A pump constructed in accordance with the present invention is generally indicated at 10 in FIG. 1. Pump 10 includes a housing 12 that is constructed to enclose the various electromechanical structures associated with pump 10. Housing 12 can be constructed of a variety of known materials, including, but to limited to, metals and plastics.

An operator control panel 14 is mounted on housing 12 and is constructed to facilitate use of pump 10. In the embodiment of the present invention depicted in FIG. 1, operator control panel 14 includes a display 16 constructed to provide a visual indication of certain operating parameters of pump 10. For example, display 16 can be an LED display of known construction and operation. Those of ordinary skill in the art will recognize that other known display technologies can be used without departing from the scope of the present invention. Display 16 preferably is configured to provide a visually-perceivable numerical and/or symbolic display which will enable a user to determine (a) the operating parameters of pump 10, e.g., time, rate, volume of fluid delivered, volume of fluid to be delivered, etc.; and/or b) the operating parameters programmed into pump 10 by the operator, thereby allowing the pump operator to confirm that the correct pumping parameters have been programmed into pump 10.

Operator control panel 14 further includes a user interface 18 that is configured to permit a user to program or otherwise operate pump 10 of the present invention. In the embodiment of the present invention depicted in FIG. 1, user interface 18 includes a plurality of buttons 20, including numerical buttons 22 and function buttons 24. It will be appreciated that user interface 18 can alternatively or additionally include switches, knobs, and other known control devices. For example, function buttons 24 can include a start/stop/hold button that allows a user to initiate, pause, or terminate a pumping regimen. In addition, function buttons 24 can include buttons that allow a user to display certain pump information, such as the amount of liquid delivered during the pumping regimen, the current pump rate, the elapsed or remaining time in the dosing regimen, and other desired operating information. Function buttons 24 also can include buttons that allow a user to program pump 10 in order to generate a desired pumping regimen. For example, function buttons 24 can include buttons that enable a user to program the pump rate and/or the volume to be pumped, as well as buttons that enable a user to select one of a plurality of preprogrammed pumping regimens. Buttons 20 also can include buttons enabling a user to deliver a bolus of liquid immediately, or at selected time during the pumping regimen. Additional pump controls can be included in user interface 18 without departing from the scope of the present invention.

User interface 18 and display 16 are electronically coupled to a central processing unit 100 that is configured to control operation of pump 10. Central processing unit (CPU) 100 preferably is configured to receive operating parameter information from user interface 18 and to control operation of pump 10 in accordance therewith. Central processing unit 100 further is configured to control display 16 so as to provide a visual indication of the operating parameter information entered by a user by way of user interface 18. Central processing unit also is configured to monitor operation of pump 10, e.g., time of operation, cycles, etc., and to control display 16 so as to provide a visual indication of the operating parameters of pump 10. The CPU 100 can be integrally located within the pump 10 as shown or can be located remote from the pump 10 and electrically connected thereto by an appropriate cable or cord.

Referring to FIGS. 1 and 2, pump 10 includes a blade 102 having a leading edge 104 having a length and a width, leading edge 104 being constructed to impart a compressive force on a tube 30 placed in a tube-receiving portion 26 of pump 10, as described in detail herein. Pump 10 also includes a first occlusion member 106 and a second occlusion member 108. First and second occlusion members 106, 108 have respective leading edges 110, 112 constructed to impart a compressive force on a tube 30 placed in tube-receiving portion 26 of pump 10, as described in detail herein. First occlusion member 106 is positioned in an upstream position relative to blade 102, while second occlusion member 108 is positioned in a downstream position relative to blade 102. Leading edges 104, 110, and 112 of blade 102, first occlusion member 106, and second occlusion member 108, respectively, are depicted in the figures as being in substantially linear alignment with one another. This relative orientation of blade 102, first occlusion member 106, and second occlusion member 108 allows for operation of pump 10 with a minimal likelihood of inadvertent kinking of a tube 30 disposed in tube-receiving portion 26. However, it will be appreciated that blade 102, first occlusion member 106, and second occlusion member 108 can be positioned with respect to one another in a variety of ways, e.g., in order to define a curved pathway for a tube 30 positioned in tube-receiving portion 26.

Central processing unit 100 is electrically coupled to motor 114 which is configured to operate a reciprocator 116 in accordance with operating parameters programmed into central processing unit 100 using user interface 18. Reciprocator 116 is constructed to impart a reciprocating motion to blade 102, first occlusion member 106, and second occlusion member 108 between the respective first and second positions of each.

As above-discussed, in their respective first positions, leading edges 104, 110, and 112 are positioned in engagement with a tube 30 positioned in tube-receiving portion 26 such that leading edges 104, 110, and 112, respectively, compress the tube at their respective first positions. In one embodiment of the present invention, leading edges 104, 110, and 112 substantially occlude flow (at their respective positions) through a tube 30 positioned in tube-receiving portion 26 when blade 102, first occlusion member 106, and second occlusion member 108 are in their respective first positions. In the respective second positions of blade 102, first occlusion member 106, and second occlusion member 108, leading edges 104, 110, and 112, respectively, do not impart a compressive force upon a tube 30 positioned within tube-receiving portion 26, thereby permitting flow through the tube at the respective positions of leading edges 104, 110, and 112.

Figure 6:
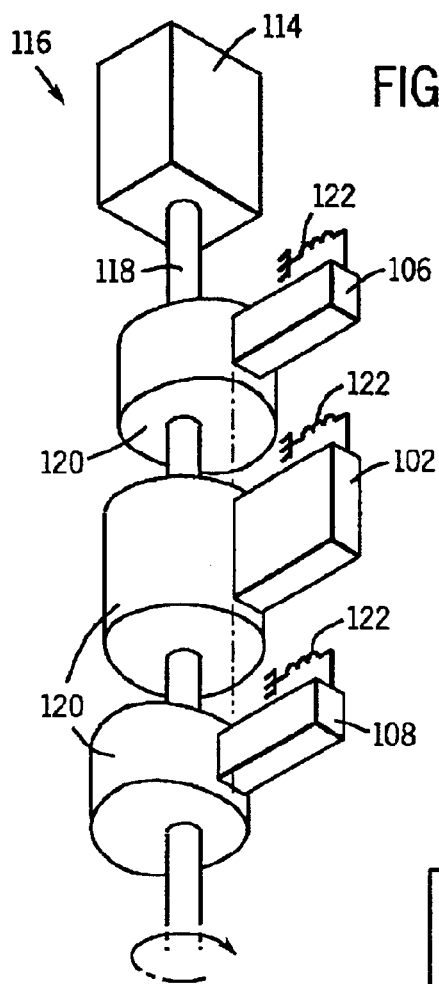
FIG. 6 is an illustration of a cam-based reciprocator configuration of the pump constructed in accordance with the present invention.

Reciprocator 116 of pump 10 can have a variety of known configurations. In one embodiment illustrated in FIG. 6, reciprocator 116 includes a shaft 118 rotationally driven by motor 114. Cam members 120 are positioned on shaft 118 to cause lateral, reciprocating movement of blade 102, first occlusion member 106, and second occlusion member 108 as shaft 118 is rotated by motor 114. Reciprocator 116 may include resilient members 122, e.g., springs, associated with each of blade 102, first occlusion member 106, and second occlusion member 108 in order to ensure the desired reciprocating movement thereof from their respective first positions to their respective second positions. However, it will be appreciated the resilience of a tube 30 positioned in tube-receiving portion 26, together with the pressure of a fluid passing through the tube, will tend to cause blade 102, first occlusion member 106, and second occlusion member 108 to move from their respective first positions to their respective second positions when cam members 120 are not urging blade 102, first occlusion member 106, and/or second occlusion 108 toward their respective first positions.

Figure 7:
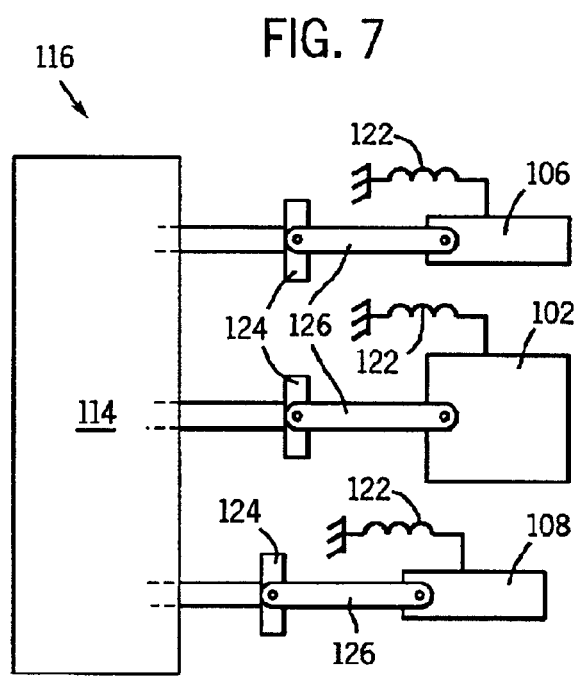
FIG. 7 is an illustration of a piston-based reciprocator configuration of the pump constructed in accordance with the present invention.

In an alternative embodiment of the present invention illustrated in FIG. 7, motor 114 and reciprocator 116 are constructed so as to provide three piston members 124, each piston member 124 being associated with one of blade 102 first occlusion member 106, and second occlusion member 108. In this embodiment, motor 114 and reciprocator 116 are constructed to selectively move the piston members 124 in a desired pattern so as to cause blade 102, first occlusion member 106, and second occlusion member 108 to move between their respective first and second positions as discussed above. In this embodiment, blade 102, first occlusion member 106, and second occlusion member 108 can be mechanically coupled to the piston members 124 by coupling member 126 so as to provide the desired reciprocating movement thereof. Alternatively, blade 102, first occlusion member 106, and second occlusion member 108 can be physically separate from the piston members 124, but positioned so as to be urged toward their respective first positions by the piston members 124. Resilient members 122 can be provided in order to urge blade 102, first occlusion member 106, and second occlusion member 108 to their respective second positions as discussed above.

Motor 114 and reciprocator 116 are constructed to move blade 102, first occlusion member 106, and second occlusion member 108 between their respective first and second positions in a predetermined sequence so as to impart a desired flow pattern through a tube 30 positioned in tube-receiving portion 26. For example, motor 114 and reciprocator 116 can be constructed to provide the following sequence of movements to blade 102, first occlusion member 106, and second occlusion member 108: (i) first occlusion member 106 and blade 102 are in their respective second positions while second occlusion member 108 is in its first position, thereby allowing fluid to flow into a tube 30 positioned within tube-receiving portion 26; (ii) first occlusion member 106 is moved to its first position while blade 102 is in its second position and second occlusion member 108 is in its first position, thereby preventing further flow of fluid into a tube 30 positioned within tube-receiving portion 26; (iii) second occlusion member 108 is moved to its second position while first occlusion member 106 is in its first position and blade 102 is in its second position, thereby allowing fluid to flow out of a tube 30 positioned within tube-receiving portion 26; (iv) blade 102 is moved to its first position while first occlusion member 106 is in its first position and second occlusion member 108 is in its second position, thereby forcing fluid to flow downstream out of a tube 30 positioned within tube-receiving portion 26; (v) second occlusion member 108 is moved to its first position while first occlusion member 106 and blade 102 are in their respective first positions; and (vi) first occlusion member 106 and blade 102 are moved to their respective second positions, thereby allowing fluid to flow into a tube 30 positioned in tube-receiving portion 26.

It is to be appreciated that the foregoing is only an example of operation of pump 10 of the present invention. In this example, first and second occlusion members 106, 108 are moved in a complementary fashion in order to prevent backflow through a tube 30 positioned within tube-receiving portion 26. One of ordinary skill in the art will recognize that various modifications of this operation pattern are possible, depending upon the desired flow characteristics through the tube.

It will be appreciated that the volume of fluid pumped through a tube 30 positioned in tube-receiving portion 26 with each movement of blade 102 into its first position will be dependent upon (i) the length and width of leading edge 104 of blade 102; and (ii) the cross-sectional dimensions of the tube. The width of leading edge 104 of blade 102 preferably is selected such that leading edge 104 substantially collapses a tube 30 positioned in tube-receiving portion 26 along a length of leading edge 104 when blade 102 is in its first position, thereby minimizing the amount of residual fluid left in the tube during each compression of the tube by blade 102. The length and width of leading edge 104 of blade 102 are selected to provide a desired range of flow volumes upon each stroke of blade 102. The length of leading edge 104 of blade 102 is preferably between about 2 cm. and about 12 cm.

In the embodiment of the present invention depicted in FIGS. 1 and 2, tube-receiving portion of the pump 10 includes a door 28 that is hingedly attached to housing 12 to allow ready access to tube 30. Tube-receiving portion 26 is constructed to receive and releasably retain a length of the tube 30 therein through which pump 10 will pump a selected fluid, as described in detail herein. Latching means 29, 31 are provided on the door 28 and the pump housing 12 to releasably maintain the door 28 in a closed position. The latching means 29, 31 can include, without limitation, magnets and metal plates or fasteners, hook or catch and latch arrangements, fabric hook and loops, etc. The latching means 29, 31 should be designed to keep the door 28 closed despite the forces imparted on the door 28 by the blade 102 and the occlusion members 106, 108, and yet allow a care giver to manually open the door 28.

As depicted in FIG. 2, housing 12 and door 28 define a first tube-access aperture 36 which is sized and configured to permit tube 30 to pass therethrough without substantially restricting the flow of fluid through tube 30. Housing 12 and door 28 further define a second tube-access aperture 38 which is sized and configured to permit tube 30 to pass therethrough without substantially restricting the flow of fluid through tube 30. It will be appreciated that first and second tube-access apertures 36, 38 can be entirely defined by housing 12 or by door 28. However, in the depicted embodiment, housing 12 and door 28 each define a portion of tube-access apertures 36, 38. First and second tube-access apertures 36, 38 can be constructed such that they are larger in diameter than the outer diameter of tube 30, and thereby ensuring that first and second tube-access apertures 36, 38 impart no compressive force on tube 30. Alternatively, first and second tube-access apertures 36, 38 can be constructed such that they are equal to or slightly smaller in diameter than the outer diameter of tube 30, thereby causing first and second tube-access apertures 36, 38 to frictionally engage tube 30 passing through tube-receiving portion 26. However, it is preferable that the frictional engagement between tube 30 and housing 12 not be so significant so as to impart more than a nominal compressive force on tube 30, thereby minimizing the effects of first and second tube-access apertures 36, 38 on the flow characteristics of a fluid pumped by pump 10 through tube 30.

In a first embodiment of pump 10 present invention, as shown in FIG. 2, door 28 defines a surface 40 constructed to substantially limit movement of tube 30 when a compressive force is applied to tube 30 by any of blade 102, first occlusion member 106, and second occlusion member 108. Surface 40 preferably is arcuate in cross-section, the arc having a diameter substantially equal to the exterior diameter of a tube 30 to be positioned in tube-receiving portion 26, thereby ensuring that surface 40 substantially prevents movement of tube 30 away from blade 102. first occlusion member 106, and/or second occlusion member 108 during operation of pump 10. The surface 40 can also be defined by an arcuate recess or elongated groove 42 formed on door 28 between first and second tube-access apertures 36, 38. The groove 42 can have a curved or flat bottom surface and opposing sides with a radius blending the bottom surface with each of the sides. The width of the groove 42 is preferably sufficient to accommodate the requisite collapsing or flattening of the tube 30 during compression by the blade 102 and occlusion members 106, 108. It will be appreciated that arcuate recess 42 defined by door 28 cannot provide more than approximately 180° of circumferential constraint for tube 30 without making it difficult for a pump operator to place tube 30 in tube-receiving portion 26 of pump 10. For this reason, a tube set 60 constructed in accordance with a second embodiment of the present invention as described below is beneficial.

In the second embodiment of pump 10 of the present invention shown in FIG. 2A, the door 28A has an interior surface 32 and an elongated cavity 34 is formed therethrough. The cavity 34 generally registers with a similar cavity 35 on the housing 12 of the pump 10. The blade 102 and the occlusion members 106, 108 register with the cavity 34 when the door 28A is closed. The door 28A defines at least one tube holder receiving slot 44 constructed to slidably and lockingly receive a corresponding number of tab members 46 associated with tube set 60 so as to ensure the proper positioning of tube set 60 within tube set receiving portion 26A of pump 10. In the depicted embodiment, two pairs of opposing tab members 46 are positioned on a base or tube holder 62 to slidably engage two pairs of L-shaped slots 44 and ensure that tube set 60 is properly positioned within tube set receiving portion 26A prior to the delivery of a fluid through tube 30. Also in this embodiment, door 28A defines an aperture 48 therethrough, the function of which will be described in detail below.

As can be understood with reference to FIGS. 1 and 2A, tube set 60 of the present invention includes tube 30 having a first end portion 52 constructed to be fluidly connected to a source of fluid to be delivered to a patient. For example, first end portion 52 may include a spike or other penetration member defining a flow channel therethrough, the penetration member being constructed to penetrate a pierceable membrane or seal fluidly sealing a fluid container. First end portion 52 also may include a luer member or other known connector useful for providing a fluid connection between tube 30 and a fluid container.

Tube 30 of tube set 60 also includes a second end portion 54 constructed to be connected directly or indirectly to a patient thereby enabling the delivery of the fluid to the patient. For example, second end portion 54 may include a catheter configured for insertion into a patient's circulatory system, or a gastrostomy or nasogastric tube constructed for insertion into a patient's gastrointestinal tract, or second end portion 54 may be configured for fluid connection to such a catheter or tube. Tube 30 can be constructed of a variety of known materials, e.g., silicone or polyvinyl_chloride (PVC). In a preferred embodiment of the present invention tube 30 is constructed from PVC.

Referring to FIGS. 2A, 3 and 4, tube set 60 further includes a base 62 having a first end portion 64 and a second end portion 66. First end portion 64 defines a first tubing aperture 68 configured to receive tube 30 therein. Second end portion 66 defines a second tubing aperture 70 configured to receive tube 30 therein. First and second tubing apertures 68, 70 preferably are configured to frictionally engage an outer surface of tube 30 to inhibit inadvertent movement of tube 30 through first and second tubing apertures 68, 70. However, first and second tubing apertures 68, 70 are also configured such that base 62 can be slid along a length of tube 30. By providing for sliding movement of base 62 along the length of tube 30 of tube set 60, it is possible to use different sections of tube 30 for pumping fluid. In this way, if blade 102, first occlusion member 106, and/or second occlusion member 108 cause a portion of tube 30 to become compromised in some way as a result of the application of compressive forces to tube 30, base 62 can be moved along tube 30 so that a separate portion of tube 30 is disposed within tube set receiving portion 26 of pump 10. Also, by providing for sliding movement of base 62 along the length of tube 30 of tube set 60, it is possible for a person utilizing tube set 60 to adjust the position of base 62 to a position that is most convenient for the intended operation of pump 10.

Base 62 defines an arcuate channel 72 therethrough between said first and second tubing apertures 68, 70. Arcuate channel 72 and first and second tubing apertures 68, 70 are substantially co-axial in the embodiment of the invention depicted herein. Arcuate channel 72 and first and second tubing apertures 68, 70 also can be oriented with respect to one another so as to cause tube 30 in tube set 60 to be curved. It will be appreciated that the respective orientations of arcuate channel 72 and first and second tubing apertures 68, 70 will be determined, at least in part, by the respective positions of blade 102, first occlusion member 106, and second occlusion member 108 of pump 10 with which tube set 60 is to be used.

Arcuate channel 72 is configured to prevent movement of tube 30 upon activation of any of blade 102, first occlusion member 106, and second occlusion member 108. The diameter or radius R of arcuate channel 72 preferably is substantially equal to the outer diameter or radius of tube 30. Arcuate channel 72 preferably surrounds 120°-340° of the circumference of tube 30 in order to inhibit movement of tube 30 upon the application of compressive forces thereto by blade 102, first occlusion member 106, and second occlusion member 108. It is not possible for arcuate channel 72 to surround 360° of the circumference of tube 30 without impairing the ability of blade 102, first occlusion member 106, and second occlusion member 108 to compress tube 30. Accordingly, a slot 74 is defined by base 62, slot 74 being configured to permit the movement of blade 102, first occlusion member 106, and second occlusion member 108 therethrough.

As above-discussed, one or more tab members 46 are formed on base 62. As best seen in FIGS. 2A and 11, tab members 46 cooperate with slots 44 on pump 10 to ensure the proper positioning and retention of tube set 60 within tube set receiving portion 26A.

As best seen in FIGS. 2A and 5, tube set 60 further includes a slide clamp 76 constructed to selectively occlude tube 30. Slide clamp 76 defines a channel 78 having a first end portion 80 and a second end portion 82. The channel 78 at first end portion 80 is configured such that tube 30 can be received therethrough without imparting a compressive force to tube 30, while the channel 78 at second end portion 82 is configured (preferably narrowed) such that tube 30 is compressed by slide clamp 76 when tube 30 is positioned within the second end portion 82 of channel 78.

Slide clamp 76 is positioned on base 62 such that it is reciprocatingly movable through aperture 48 defined by door 28A. Slide clamp 76 slides within a hole 77 formed through the first end portion 64 of the base 62. The slide clamp 76 is preferably longer than the depth of the first end portion 64. The slide clamp 76 slidably inserts into hole 77 so that the first end portion 80 of the channel 78 registers with the first tubing aperture 68. Then the tube 30 is inserted through the aperture 68 and the first end portion 80 of the channel 78. Preferably in this position of the slide clamp 76 its upper surface is substantially flush with the upper surface of the base 62, and the lower surface of the slide clamp 76 protrudes from the lower surface of the base 62 as shown in FIG. 9. The slide clamp 76 is then pushed forward or upward in the hole 77 to occlude the tube 30 as shown in FIG. 8. In this position both the upper and lower surfaces of the slide clamp 76 protrude to some extent from the base 62.

An oblong recess 50 in the door 28A around the aperture 48 receives the portion of the slide clamp 76 that protrudes below the base and allows the tube set 60 to be placed in the cavity 34 where the slots 44 receive the tabs 46. The tube set 60 is then slid downward in FIGS. 2A and 11 so that the slots 44 constrain the tabs 46 and thereby retain the tube set 60 in the cavity 34 of the door 28A. Once the occluded tube set 60 is releasably secured to the door 28A in this manner, the slide valve 76 is registered with the aperture 48 and the user can push the slide valve 76 toward the rear of the door 28A to open the tube 30. The user then swings the door 28A shut against the pump housing 12. The latching means 29, 31 keep the door 28A closed until the user is ready to open it. Advantageously, the user can still slide the tube 30 longitudinally within the tube set 60 to adjust slack and avoid excessive repeated compressive cycling of a given length of the tube 30. In order to prevent free flow of fluid through tube 30 when tube set 60 is positioned within tube set receiving portion 26A, at least one of blade 102, first occlusion member 106, and second occlusion member 108 is preferably in its first position.

To remove the tube set 60 from the pump 10, the user presses the slide valve 76 down (toward the pump housing 12) into the aperture 48, as shown in FIG. 10, which occludes the tube 30 by forcing it into the narrowed second end portion 82. A recess 56 in the cavity 35 of the pump housing 12 accommodates this movement of the slide valve 76. Then the door 28A can be opened and the tube set 60 removed or replaced. Slide clamp 76 preferably is constructed such that tube set 60 can be installed in tube set receiving portion 26A of pump 10 with tube 30 in the second end portion 82 of channel 78, thereby preventing free flow of fluid through tube 30.

Slide clamp 76, aperture 48, slots 44 and tab members 46 cooperate with each other in order to prevent removal of tube set 60 from pump 10 unless slide clamp 76 is in a position to occlude flow through tube 30. That is, when tube 30 is positioned in the first end portion 80 of channel 78, a portion of slide clamp 76 is disposed through aperture 48. It will be appreciated that tab members 46 cooperate with L-shaped slots 44 to permit base 62 to be moved only in a direction parallel to a longitudinal axis of the tab members 46 and slots 44. However, because slide clamp 76 is configured to move in a direction substantially perpendicular to the direction of motion permitted by tab members 46 and slots 44, slide clamp 76 prevents tube set 60 from being removed from tube set receiving portion 26A while flow is still possible through tube 30. Thus, in order to withdraw tube set 60 from tube set receiving portion 26A, it is necessary to apply a force to slide clamp 76, thereby urging slide clamp 76 through aperture 48, which simultaneously urges tube 30 into said second end portion 82 of channel 78, thereby occluding flow through tube 30. Once tube 30 is properly positioned within second end portion 82 of channel 78, tube set 60 can be withdrawn from tube set receiving portion 26A. It also will be appreciated that tube set 60 cannot be properly positioned in tube set receiving portion 26A unless tube 30 is positioned within second end portion 82 of channel 78 due to the relative orientations and functions of slide clamp 76, aperture 48, tab members 46, and slots 44.

It is to be appreciated that pump 10 of the present invention is intended to be used in the delivery of a wide variety of fluids to a patient, including both the delivery of enteral nutritional products into a patient's gastrointestinal tract and the delivery of parenteral products into a patient's vascular system.

Although the present inventions have been described herein in connection with certain exemplary embodiments, it is anticipated that certain modifications will be evident to those of ordinary skill in the art, such modifications being within the scope of the appended claims.

What is claimed is:
1. A tube set comprising:
an elongated tube of a given diameter and circumference; and
a base having a first end portion and a second end portion, said first end portion defining a first tube-receiving aperture therethrough, said second end portion defining a second tube-receiving aperture therethrough, said first and second tube-receiving apertures constructed to receive and permit sliding of a length of the tube therethrough;
said base further defining an arcuate compression surface extending 120–340 degrees circumferentially around the diameter of the tube and adapted to engage the circumference of a portion of the length of the tube located between the first tube receiving aperture and the second tube receiving aperture, said base constructed for insertion into a tube set receiving portion of a pump.

2. A tube set in accordance with claim 1, further comprising a slide clamp constructed to selectively restrict flow through paid tube, said slide clamp slidably mounted on said base, said slide clamp defining a channel therethrough, said tube disposed within said channel defined by said slide clamp, said channel having a first end portion and a second end portion, said first end portion of said channel configured so as not to compress said tube when said tube is disposed therein, said second end portion of said channel configured to compress said tube when said tube is disposed therein, whereby flow through said tube is at least substantially occluded when said tube is disposed in said second end portion of said channel.

3. A tube set in accordance with claim 1, wherein said base comprises at least one tab member for slidably engaging at least one slot on said tube set receiving portion of a pump.

4. A tube set in accordance with claim 3, wherein said at least one tab member is substantially planar and extends substantially parallel to said first and second tube-receiving apertures.

5. A tube set in accordance with claim 3, further comprising a slide clamp constructed to selectively restrict flow through said tube, said slide clamp defining a channel therethrough, said tube disposed in said channel defined by said slide clamp, said slide clamp constructed to be slidable through an aperture defined by a tube set receiving portion of a pump between a first position in which said slide clamp protrudes into an aperture defined by a tube set receiving portion of a pump and a second position in which said clamp does not protrude into an aperture defined by a tube set receiving portion of a pump, said slide clamp constructed to limit slidable movement of said at least one tab member in at least one slot on a tube set receiving portion of a pump and thereby prevent removal of said tube set from a tube set receiving portion of a pump when said slide clamp is in said first position, said slide clamp constructed to permit slidable movement of said at least one tab member in at least one slot on a tube set receiving portion of a pump when said slide clamp is in said second position and thereby permit removal of said tube set from a tube set receiving portion of a pump when said slide clamp is in said second position.

6. A tube set in accordance with claim 5, wherein said channel defined by said slide clamp has a first end portion and a second end portion, said first end portion of said channel configured so as not to compress said tube when said tube is disposed therein, said second end portion of said channel configured to compress said tube when said tube is disposed therein, whereby flow through said tube is at least substantially occluded when said tube is disposed in said second end portion of said channel, wherein said tube is disposed in said second end portion of said channel when said slide clamp is in said second position thereof, and wherein said tube is disposed in said first end portion of said channel when said slide clamp is in said first position thereof.

7. A tube set in accordance with claim 1, wherein said tube comprises a first end constructed for fluid communication with a fluid source, and wherein said tube comprises a second end constructed to deliver a fluid to a patient.

* * * * *

UNITED STATES PATENT AND TRADEMARK OFFICE
CERTIFICATE OF CORRECTION

PATENT NO. : 6,942,473 B2
DATED : September 13, 2005
INVENTOR(S) : Kent Abrahamson et al.

It is certified that error appears in the above-identified patent and that said Letters Patent is hereby corrected as shown below:

Column 10,
Line 21, after "through" delete "paid" and insert -- said --.

Signed and Sealed this

Third Day of January, 2006

JON W. DUDAS
*Director of the United States Patent and Trademark Office*